United States Patent
Grote et al.

(10) Patent No.: US 6,526,837 B1
(45) Date of Patent: Mar. 4, 2003

(54) SCREW ACTION GRIP WITH ADJUSTABLE STIFFNESS AND ALIGNMENT GUIDES

(75) Inventors: Vogel P. Grote, Jordan, MN (US); Douglas K. Hansen, Bloomington, MN (US); Michael E. Bloom, Oak Grove, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 09/513,253

(22) Filed: Feb. 24, 2000

(51) Int. Cl.[7] ............................................. G01N 3/02
(52) U.S. Cl. ...................................................... 73/856
(58) Field of Search .......................... 73/7, 103, 856, 73/860, 849, 853, 847, 82, 81, 83, 862.69, 779; D24/32

(56) References Cited

U.S. PATENT DOCUMENTS

| | | | | |
|---|---|---|---|---|
| 5,297,441 A | * | 3/1994 | Smith et al. ................... | 73/860 |
| 5,511,432 A | * | 4/1996 | Holmes ........................ | 73/856 |
| 5,877,432 A | * | 3/1999 | Hartman et al. .......... | 73/862.39 |
| 5,945,607 A | * | 8/1999 | Peppel et al. ................. | 73/856 |
| 6,247,356 B1 | * | 6/2001 | Merck, Jr. et al. .............. | 73/82 |

OTHER PUBLICATIONS

Catalog: "Grips and Jaw Faces", Instron Direct, p. 43.

Catalog: "Side Acting Mechanical Grips", Instron Direct, p. 6–3.

* cited by examiner

Primary Examiner—Max Noori
(74) Attorney, Agent, or Firm—Westman, Champlin & Kelly, P.A.; S. Koehler

(57) ABSTRACT

A test specimen holder for holding a test specimen in a material testing machine includes screw operated actuators with removable blocks of material. Preferably, a plurality of blocks of material is provided with a varying degree of compliance. Alignment guides indicating the relative position of jaw plates are also provided.

19 Claims, 6 Drawing Sheets

SCREW ACTION GRIP WITH ADJUSTABLE
STIFFNESS AND ALIGNMENT GUIDES

BACKGROUND OF THE INVENTION

The present invention relates to a material testing system that applies loads to a test specimen. More particularly, the present invention relates to a test specimen holder that holds the test specimen in the material testing system.

Test specimen holders are well known and are used frequently to hold a test specimen in a material testing system. Various types of test specimen holders have been advanced, which include hydraulically operated and mechanically operates wedge grips having opposed jaws. These types of test specimen holders are generally used on test specimens that can withstand the high clamping forces provided by the wedge jaws. Other test specimen holders have been advanced to hold more fragile test specimens. In one known type, screw operated actuators are positioned on opposite sides of the test specimen. Each of the screw actuators displace a jaw plate toward the other with the test specimen disposed therebetween.

The screw operated actuators also have shortcomings. For instance, misalignment of the test specimen is possible when screw actuators used in an upper grip and the screw actuators used in a lower grip are not positioned correctly with respect to the tension/compression axis of the material testing system. In addition, a reduction in clamping pressure can arise over time due to deformation of the test specimen during the test. A screw operated test specimen holder that addresses one or both of these shortcomings is therefore desired.

SUMMARY OF THE INVENTION

A first broad aspect of the present invention is a test specimen holder for holding the test specimen in a material testing machine. The test specimen holder includes a base member having an end coupleable to the material testing machine and a pair of first and second aligned, spaced apart support members. Each support member includes indicia. A pair of movable jaw assemblies are provided. A first movable jaw assembly is slidably coupled to the first support member, while the second movable jaw assembly is slidably coupled to the second support member. Each movable jaw assembly includes an indicator slidable therewith and disposed proximate the indicia of the corresponding support member.

A second broad aspect of the present invention includes a test specimen holder having a base member with an end coupleable to the material testing machine and a pair of first and second aligned, spaced apart support members. A movable jaw assembly is a adapted for each of the support members. Each jaw assembly includes a jaw plate engageable with a test specimen and an actuator adapted to selectively move the jaw plate. A first and second plurality of blocks of material are provided. Each plurality includes blocks of material of different compliance. Each block of material is adapted to be inserted between one of the actuators and the corresponding jaw plate.

DETAILED DESCRIPTION OF THE
ILLUSTRATIVE EMBODIMENTS

Figure 1:
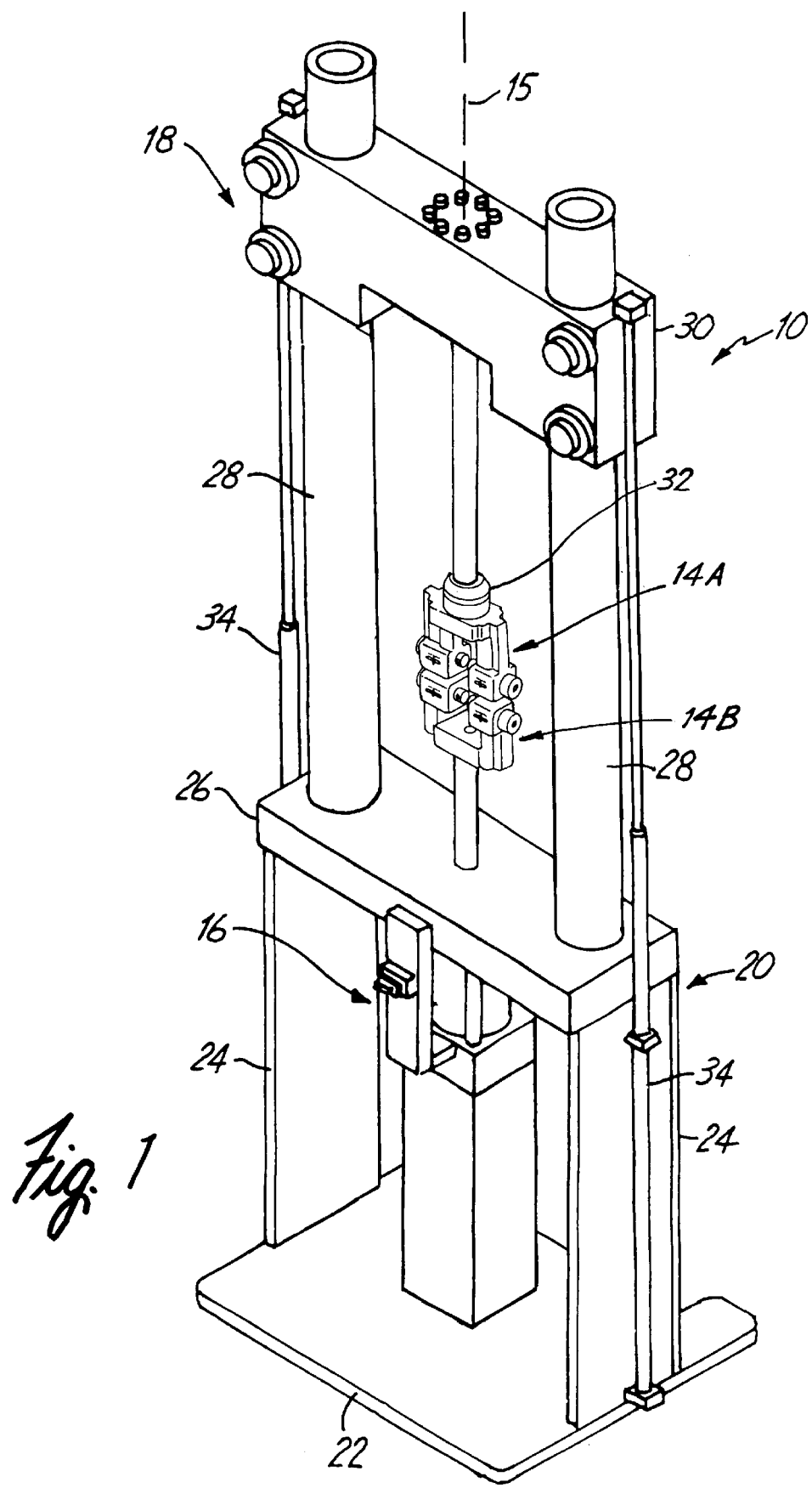
FIG. 1 is a perspective view of a material testing system having test specimen holders of the present invention.
Figure 4:
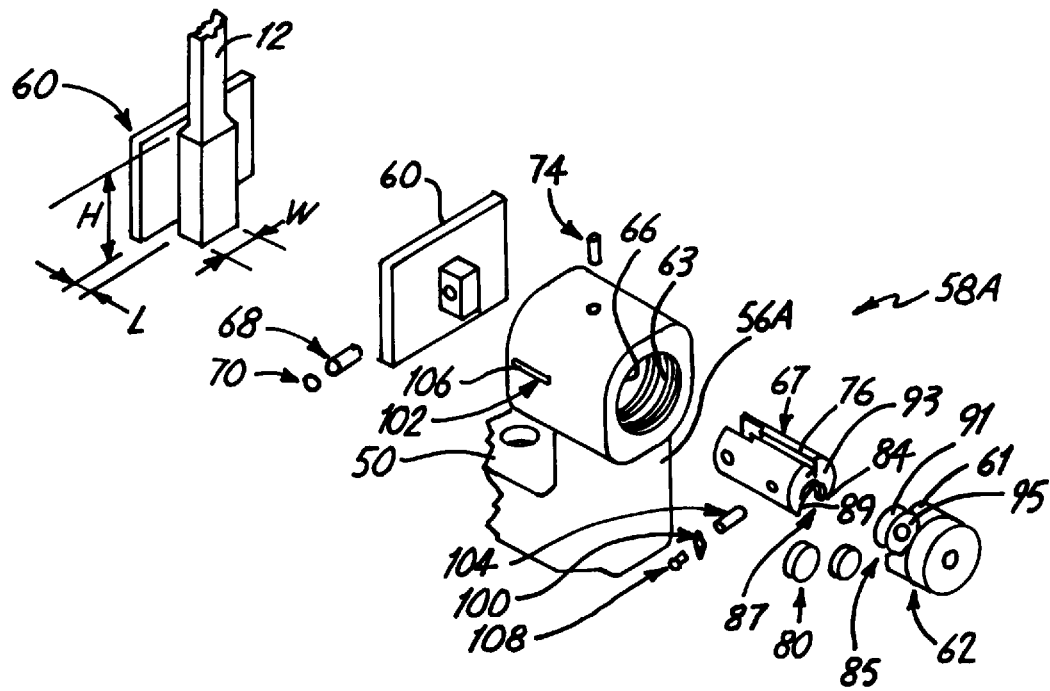
FIG. 4 is an exploded perspective view of a portion of the test specimen holder.

FIG. 1 illustrates a exemplary material testing system 10 for applying loads to a test specimen 12 (FIG. 4). The system 10 includes an upper grip 14A and a lower grip 14B of the present invention that hold the test specimen 12 along a longitudinal axis 15. The lower grip 14B is connected to an actuator 16 through which loads are applied to the test specimen 12 and reacted against a reaction structure generally indicated at 18. In the embodiment illustrated, the material testing system 10 includes a frame 20 having a base 22. A pair of support members 24 extend upwardly from the base 22 and are joined together by a crossbeam 26, which provides a stable support surface. A pair of support columns 28 extend upwardly from the crossbeam 26 to a movable crosshead 30. A load cell 32 joins the upper grip 14A to the crosshead 30. As is known in the art, the load cell 32 provides a representative signal indicative of tension/compressive forces applied to the test specimen 12. The crosshead 30 and the support columns 28 provide the reaction structure 18. Hydraulic lifts 34 move the crosshead 30 to selectively fixed positions. As appreciated by those skilled in the art, the system 10 less the upper grip 14A and 14B can take many forms. For instance, electric or pneumatic actuators (linear or rotary) can be used. Likewise, a fixed crosshead or a crosshead moved by other means, such as screw actuators, can be used.

Figure 2:
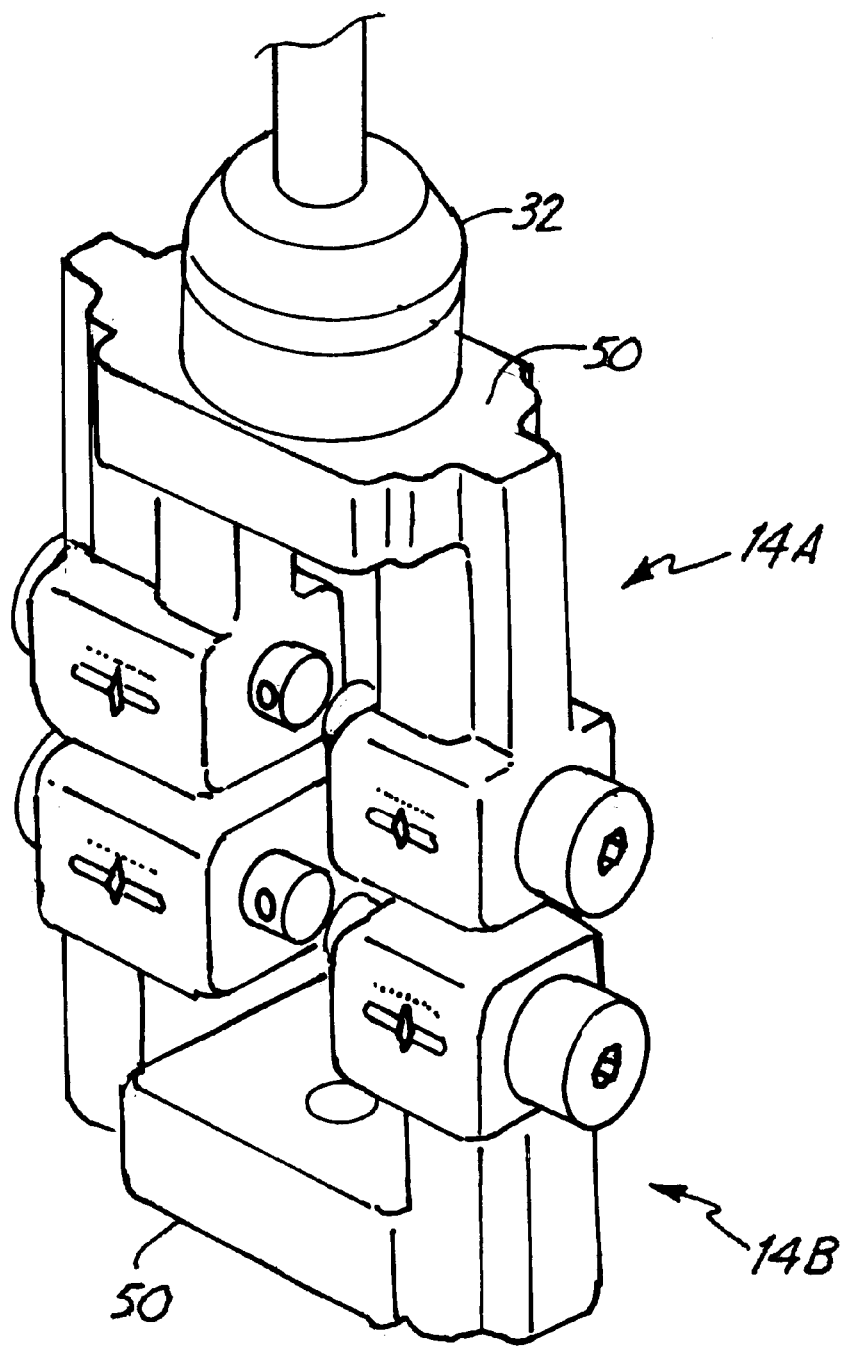
FIG. 2 is an enlarged perspective view of a pair of the test specimen holders.
Figure 3:
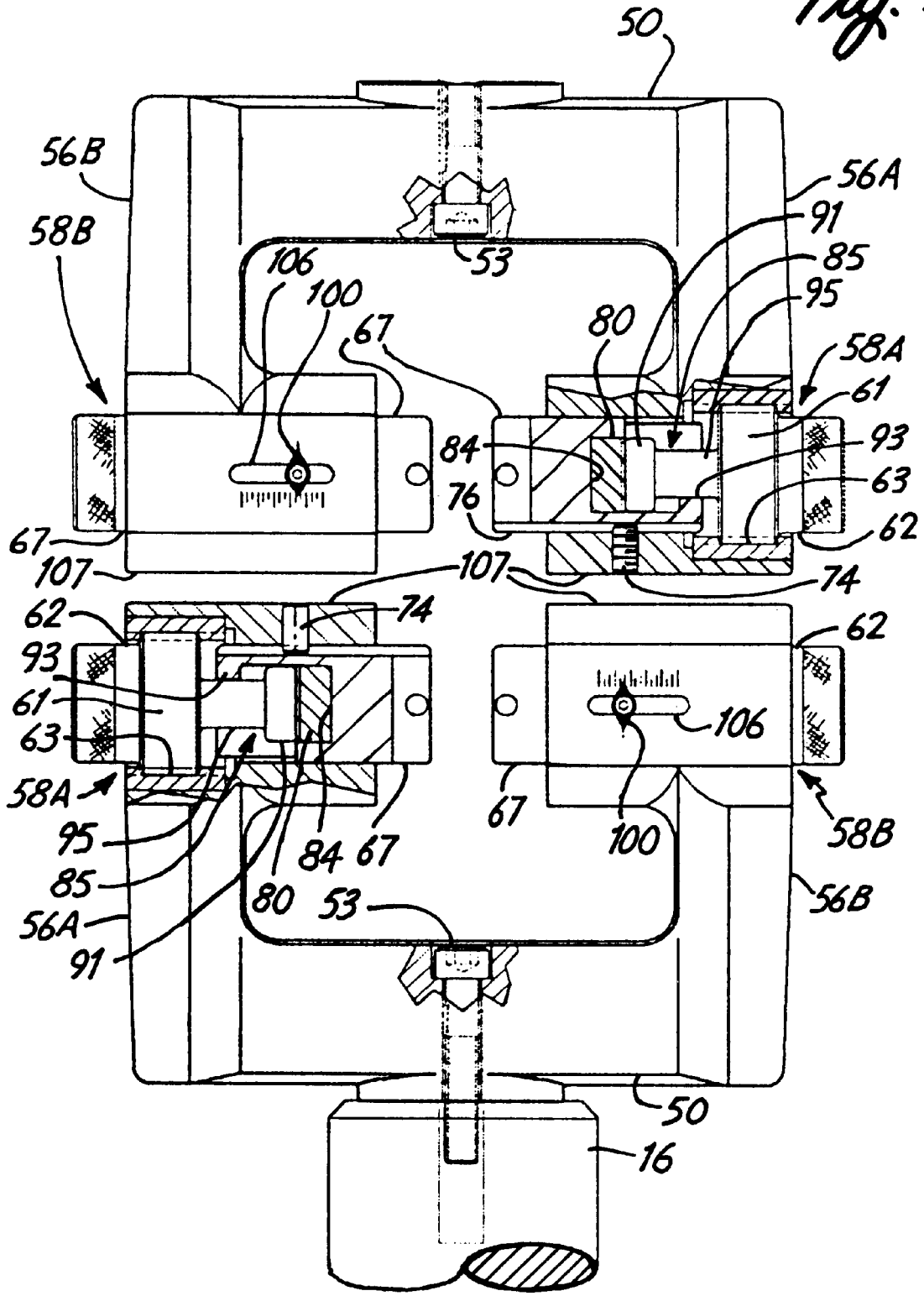
FIG. 3 are partial sectional views of the test specimen holders.

Typically, the upper and lower grips 14A and 14B are identical. Referring to FIGS. 2–4, each of grips 14A and 14B includes a base member 50 having an end 52 coupleable to a portion of the material test system 10 with a suitable fastener 53. The base member 50 includes a pair of aligned, spaced-apart support members 56A and 56B. The support member 56A is adapted to support a movable jaw assembly 58A, while the support member 56B is adapted to support a movable jaw assembly 58B. Each jaw assembly 58A and 58B includes a jaw plate 60 (FIG. 4) and an actuator 62 adapted to selectively move the jaw plate 60. In the embodiment illustrated, the actuator 62 comprises a screw actuator having a threaded plug or screw 61 adapted to mate with threads 63 provided on an end of the corresponding support member 56A and 56B. In one embodiment, the support members 56A and 56B each include a through bore 66 wherein remote ends of the support members 56A and 56B furthest from the jaw plate 60 receive the screw plug 61. The actuator 62 engages a push rod 67 that is joined to the jaw plate 60. Preferably, the jaw plate 60 is removably coupled to the push rod 67, herein with a pivot pin 68, and an o-ring 70, although other forms of fasteners can be used. Likewise, a fixed connection can be provided between the guide plate 60 and the push rod 67.

In the embodiment illustrated, a guide pin 74 extends into the bore 66. A channel 76 formed in the push rod 67 receives the guide pin 74 to react any moments developed by the actuator 62 due to rotation of the screw plug 61.

As appreciated by those skilled in the art, other configurations of the support members 56A and 56B that do not require a bore 66 are possible. For instance, the support members 56A and 56B could merely be a support surface wherein the jaw plate 60 is guided and retained on the support surface.

In one aspect of the present invention, a removable block of material 80 is disposed between the screw plug 61 and the jaw plate 60. In the embodiment illustrated, the block of material 80 is disposed between the push rod 67 and the screw plug 61. The screw plug 61 contacts the removable block of material 80, which in turn, displaces the jaw plate 60 to apply the clamping load. In one embodiment, the removable block of material 80 is compliant in order that some clamping energy is stored therein so that clamping load is maintained, even upon deformation of the test specimen 12 due to the clamping load, which may occur over time. In other words, in the event the test specimen 12 was to slightly deform, the compliant block of material 80 slightly displaces the jaw plate 60 in order to substantially maintain the desired clamping load.

In a further preferred embodiment as illustrated in FIG. 4, a plurality of blocks of material 80 of different compliance are provided. Each block of material 80 is adapted to be inserted between the actuator screw plug 61 and the corresponding push rod 67. In this manner, the operator can select the block of material with the appropriate amount of compliance. In the embodiment illustrated, a recess 84 is provided and adapted to receive the block of material 80 (herein, for example, a disk or puck shaped block of material). The recess 84 opens to an end of the push rod 67 to receive a plunger 85. In particular, an aperture 87 includes a first portion 89 to receive a driver head 91 of the plunger 85 and a second, smaller portion 93 to receive a shaft 95 of the plunger 85. This construction allows the screw plug 61 with a plunger 85 to be removed, while the push rod 67 remains in support member 56A.

Figure 5:
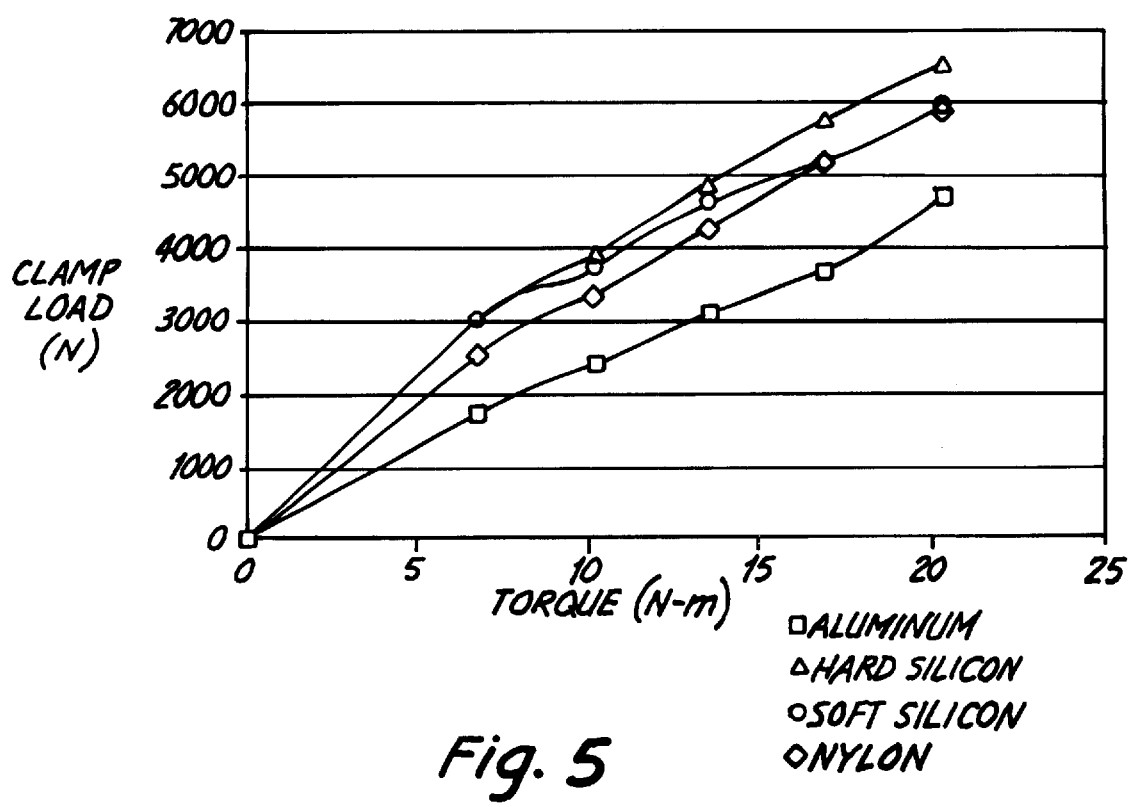
FIG. 5 is a graph illustrating clamping load versus actuator torque for various blocks of material used in the test specimen holder.

Generally, the block of material 80 is chosen as a function of teat specimen stiffness. FIG. 5 graphically illustrates clamping load versus torque for a plurality of blocks of material, herein soft silicon, hard silicon, nylon and aluminum. Table I below is for a 2000 Newton grip, showing which of block of material 80 to use for a given specimen's stiffness and the type of test "fixed" or "non-fixed" being conducted.

TABLE I

| Typical | Specimen Stiffness N/m | | Block of |
|---|---|---|---|
| Specimen | at least | but less than | Material |
| NonFixed | | | |
| Delicate | 77,100 | 583,200 | Soft Silicon |
| Soft plastic | 583,200 | 21,256,800 | Hard Silicon |
| Hard plastic | 21,256,800 | 31,130,400 | Nylon |
| Aluminum | 31,130,400 | and greater | Aluminum |
| Fixed | | | |
| Delicate | 15,603,700 | 15,857,700 | Soft Silicon |
| Soft plastic | 15,857,700 | 26,193,600 | Hard Silicon |

TABLE I-continued

| Typical | Specimen Stiffness N/m | | Block of |
|---|---|---|---|
| Specimen | at least | but less than | Material |
| Hard plastic | 26,193,600 | 31,130,400 | Nylon |
| Aluminum | 31,130,400 | and greater | Aluminum |

Referring to FIG. 4, the tests specimen's stiffness (K) can be calculated according to the following equation:

$$K = A \times E / L$$

where A is the area of contact (H×W) of the test specimen 12 upon the jaw plate 60, E is the specimen modulus, and L is the specimen thickness. In a "fixed" mode, only one of the actuators 62 (either on the support member 56A or the support member 56B) is adjusted for installing or removing the test specimen 12. The actuator 62 that is adjusted receives the block of material 80, for example, as stipulated by Table I, while the other actuator 62, which is not being adjusted, uses the most rigid block of material 80, herein made of aluminum. In the "non-fixed" mode, the same block of material 80 specified or ascertained based on the stiffness of the test specimen 12 is provided in both of the support members 56A and 56B. The "fixed" mode of operation is used when extra follow-through (automatic movement of the jaw plate 60 to maintain clamping load due to spring effect of the block of material 80) is not needed, or when many test specimens 12 of the Same thickness are being tested in series. The "non-fixed" mode of operation is used when additional follow-through is needed.

A second broad aspect of the present invention includes providing an indicator 100 that moves with each corresponding jaw plate 60 for each of the jaw assemblies 58A and 58B in the support members 56A and 56B. Preferably, the indicator 100 is positioned proximate reference indicia 102 that allows the user to easily ascertain the position of the jaw plate 60 relative to the support members 56A and 56B and, thus, to the longitudinal axis 15 (FIG. 1) of the material testing system 10. In view that each of the actuators 62 are movable, it is possible that the test specimen 12, when mounted in the material test system 10, can be misaligned with respect to the longitudinal axis 15, thereby causing unintended moments to be applied to the test specimen 12. The reference indicia 102 on each of the support members 56A and 56B are mounted or otherwise disposed on the support members 56A and 56B so that when the test specimen holders 14A and 14B are mounted in the material test system 10, the longitudinal axis 15 is equally spaced from each of the reference indicia 102. In the embodiment illustrated, the indicator 100 is joined to the push rod 67 of the jaw plate 60 to move therewith. For the tubular support members 56A and 56B herein illustrated, the indicator 100 is mounted to a stand off 104 that extends through a corresponding slot 106 provided in each of the support members 56A and 56B. A suitable fastener, such as a set screw 108, can be used to join the indicator 100 to the stand off 104. Although the reference indicia 102 and corresponding indicators 100 disposed on side surfaces of each of the support members 56A and 56B, it should be noted other surfaces, such as horizontal surfaces 107 can also be used.

Figure 6:
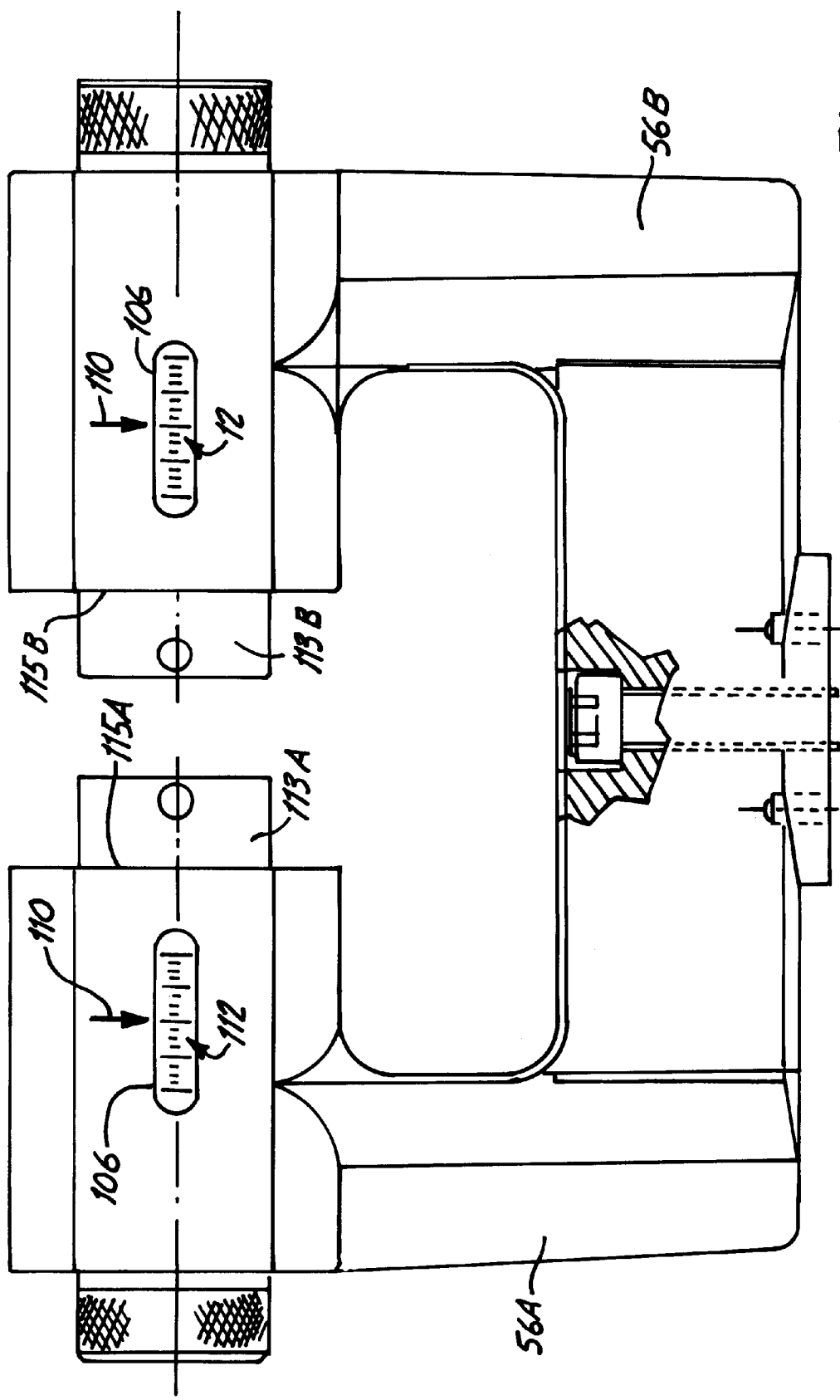
FIG. 6 is a front elevational view of a second embodiment of a test specimen holder with a portion removed.

In an alternative embodiment, illustrated in FIG. 6, indicator 110 is mounted or otherwise disposed on each of the support members 56A and 56B proximate a corresponding slot 106. Reference indicia 112 are mounted to or otherwise disposed on exterior surfaces of each of the push rods 67 to move therewith and are visible through the corresponding slots 106. If desired, the reference indicia 112 could also be located on an end portions 113A and 113B of each of the push rods 67. The indicators 110 can then extend from the support members 56A and 56B, or simply be the end face 115A and 115B of the corresponding support members 56A and 56B.

Figure 7:
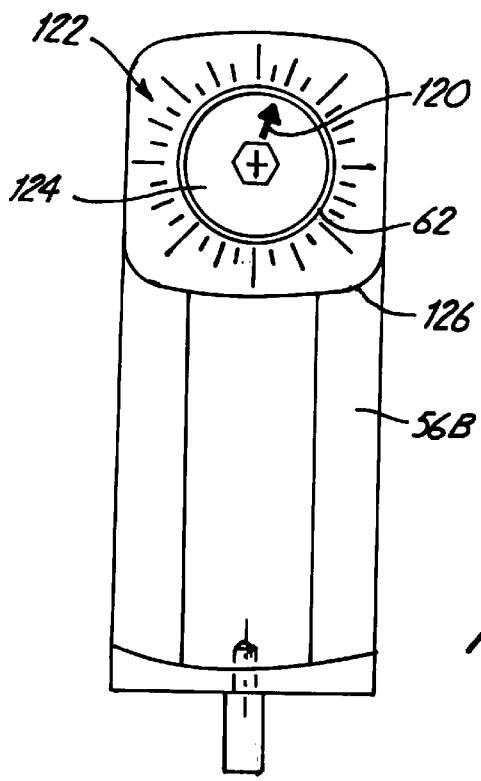
FIG. 7 is a side elevational view of a third embodiment of a test specimen holder.
Figure 8:
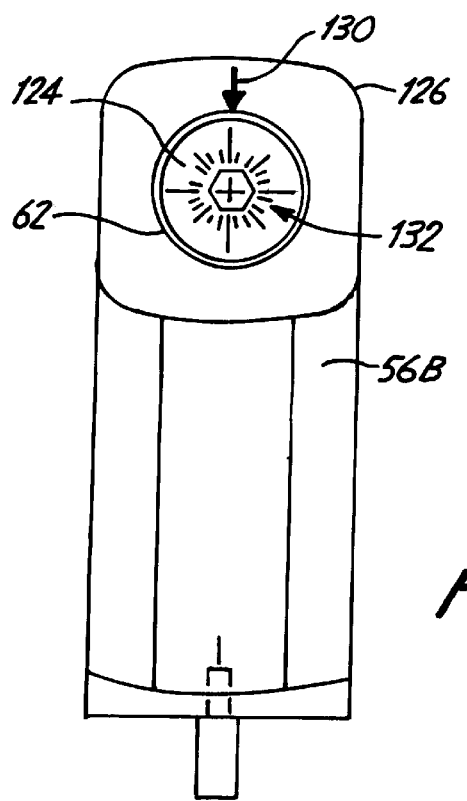
FIG. 8 is a side elevational view of a fourth embodiment of a test specimen holder.

In another embodiment, illustrated in FIG. 7, indicator 120 is mounted to or otherwise disposed on end surface 124 of each actuator 62. Reference indicia 122 are mounted to or otherwise disposed on surface 126 of support member 56A and 56B proximate each of the indicators 120, Rotation of actuator 62 can then be measured as indicator 120 points to various indicia In a further embodiment, illustrated in FIG. 8, indicator 130 is mounted to or otherwise disposed on surface 126 of support members 56A and 56B. Reference indicia 132 are mounted to or otherwise disposed on end surface 124 of each actuator 62 proximate indicator 130. The relative position of indicator 130 can then be measured with respect to indicia 132 as actuator 62 rotates to affect movement of jaw plate 60.

Although the present invention has been described with reference to preferred embodiments, workers skilled in the art will recognize that changes may be made in form and detail without departing from the spirit and scope of the invention.

What is claimed is:

1. A test specimen holder for holding a test specimen in a material testing machine applying force loads, the test specimen holder comprising:
   a base member having an end coupleable to the material testing machine and a pair of first and second aligned, spaced apart support members;
   a pair of movable jaw assemblies, wherein a first movable jaw assembly is slidably coupled to the first support member and the second movable jaw assembly is slidably coupled to a second support member; and
   wherein reference indicia and an indicator movable relative to the reference indicia are provided for each of the support members and corresponding movable jaw assemblies.

2. The test specimen holder of claim 1 wherein each support member comprises a housing having a bore, and wherein the first movable jaw assembly slides within the bore of the first support member and the second movable jaw assembly slides within the bore of the second support member.

3. The test specimen holder of claim 1 wherein each support member includes the reference indicia and each movable jaw assembly includes the corresponding indicator disposed proximate the reference indicia of the corresponding support member.

4. The test specimen holder of claim 1 wherein each support member includes the indicator and each movable jaw assembly includes the reference indicia disposed proximate the indicator of the corresponding support member.

5. The test specimen holder of claim 3 wherein the reference indicia is disposed on an outer surface.

6. The test specimen holder of claim 5 wherein each support member includes a slot opening to the corresponding bore, and wherein the reference indicia is disposed proximate the slot, and wherein each movable jaw includes a standoff extending through the slot, the standoff supporting the corresponding indicator.

7. The test specimen holder of claim 4 wherein the indicator is disposed on an outer surface of each of the support members.

8. The test specimen holder of claim 4 wherein each support member includes a slot opening to the corresponding bore, and wherein the indicator is disposed proximate the slot, and wherein each movable jaw includes reference indicia visible through the slot.

9. The test specimen holder of claim 2 wherein a remote end of each bore furthest from the other support member includes threads, and wherein the movable jaw assembly includes an actuator screw having threads mating with the threads of the bore, wherein rotation of the actuator screw moves a corresponding jaw plate of the jaw assembly relative to the corresponding support member.

10. The test specimen holder of claim 9 wherein each movable jaw assembly includes a removable block of material disposed between the jaw plate and the actuator screw.

11. The test specimen holder of claim 2 wherein each movable jaw assembly comprises:
    a jaw plate having a portion slidable in the bore;
    an actuator screw having threads engaging corresponding threads of the support member; and
    a removable block of material disposed between the actuator screw and the portion of the jaw plate.

12. The test specimen holder of claim 11 and further comprising:
    a first plurality of blocks of material for the first support member and a second plurality of blocks of material for the second support member, wherein each plurality includes blocks of material of different compliance.

13. The test specimen holder of claim 12 wherein at least some of the blocks of material for each plurality are selected from a group comprising silicon, nylon and aluminum.

14. A test specimen holder for holding a test specimen in a material testing machine applying force loads, the test specimen holder comprising:
    a base member having an end coupleable to the material testing machine and a pair of first and second aligned, spaced apart support members, each support member including threads defining a bore; and
    a pair of movable jaw assemblies, each jaw assembly adapted for one of the support members, each jaw assembly comprising:
    a jaw plate having a portion slidable in the corresponding bore of the support member;
    an actuator screw having threads engaging corresponding threads of the support member; and
    a removable block of compliant material disposed between the actuator screw and the portion of the jaw plate.

15. The test specimen holder of claim 14 and further comprising:
    a first plurality of blocks of material for the first support member and a second plurality of blocks of material for the second support member, wherein each plurality includes blocks of material of different compliance.

16. The test specimen holder of claim 15 wherein at least some of the blocks of material for each plurality are selected from a group comprising silicon, nylon and aluminum.

17. A test specimen holder kit comprising:
    a base member having an end coupleable to a material testing machine and a pair of first and second aligned, spaced apart support members;
    a pair of movable jaw assemblies, each jaw assembly adapted for one of the support members, each jaw assembly comprising:
    a jaw plate engageable with a test specimen; and
    an actuator adapted to selectively move the jaw plate; and a first plurality of blocks of material and a second plurality of blocks of material, wherein each plurality includes blocks of material of different compliance, and wherein each block of material is adapted to be inserted between one of the actuators and the corresponding jaw plate.

18. The test specimen holder kit of claim 17 and further comprising:
 a second base member having an end coupleable to the material testing machine and a pair of third and fourth aligned, spaced apart support members;
 a second pair of movable jaw assemblies, each jaw assembly adapted for one of the support members of the second base member, each jaw assembly comprising:
  a jaw plate engageable with a test specimen; and
  an actuator adapted to selectively move the jaw plate; and
  a third plurality of blocks of material and a fourth plurality of blocks of material, wherein each of the third and fourth pluralities includes blocks of material of different compliance, and wherein each block of material is adapted to be inserted between one of the actuators and the corresponding jaw plate.

19. The test specimen holder kit of claim 18 wherein at least some of the blocks of material for each plurality are selected from a group comprising silicon, nylon and aluminum.

* * * * *